United States Patent [19]

Hancock et al.

[11] Patent Number: 5,716,825
[45] Date of Patent: Feb. 10, 1998

[54] INTEGRATED NUCLEIC ACID ANALYSIS SYSTEM FOR MALDI-TOF MS

[75] Inventors: William S. Hancock, Hillsborough; John A. Chakel, San Mateo; James A. Apffel, Palo Alto; Kay Lichtenwalter, San Jose, all of Calif.

[73] Assignee: Hewlett Packard Company, Palo Alto, Calif.

[21] Appl. No.: 551,501

[22] Filed: Nov. 1, 1995

[51] Int. Cl.$^6$ .................. C12M 1/38; C12M 1/40
[52] U.S. Cl. .................. 435/286.5; 435/287.2; 435/287.9; 435/288.4; 250/288; 422/68.1
[58] Field of Search .................. 435/6, 91.2, 286.1, 435/286.5, 287.2, 287.9, 288.3, 288.4, 288.7, 808; 250/288; 422/68.1, 100, 101, 102

[56] References Cited

U.S. PATENT DOCUMENTS

| | | | |
|---|---|---|---|
| 4,891,120 | 1/1990 | Sethi et al. | 204/299 |
| 4,908,112 | 3/1990 | Pace | 204/299 |
| 5,132,012 | 7/1992 | Miura et al. | 210/198.2 |
| 5,194,133 | 3/1993 | Clark et al. | 204/299 |
| 5,252,294 | 10/1993 | Kroy et al. | 422/102 |
| 5,304,487 | 4/1994 | Wilding et al. | 435/291 |
| 5,308,978 | 5/1994 | Cottrell et al. | 250/288 |
| 5,498,545 | 3/1996 | Vestal | 436/47 |
| 5,500,071 | 3/1996 | Kaltenbach et al. | 156/272.8 |
| 5,587,128 | 12/1996 | Wilding et al. | 422/68.1 |

FOREIGN PATENT DOCUMENTS

| | | | |
|---|---|---|---|
| 62-284256 | 12/1987 | Japan | 250/288 |
| 94/05414 | 3/1994 | WIPO . | |
| WO94/28418 | 5/1994 | WIPO | 33/543 |

OTHER PUBLICATIONS

Eggers et al., "A Microchip for Quantitative Detection of Molecules Utilizing Luminescent and Radioisotope Reporter Groups", BioTechniques, vol. 17, No. 3, pp. 516–524 (1994).

Eggers and Ehrlich, "A Review of Microfabricated Devices for Gene-Based Diagnostics", Hematologic Pathology, vol. 9, No. 1, pp. 1–15 (1995).
Gusev et al., "Thin-Layer Chromatography Combined with Matrix-Assisted Laser Desorption/Ionization Mass Spectrometry", Anal. chem., vol. 67, No. 11, pp. 1805–1814 (1995).
Limbach, et al., "Characterization of Oligonucleotides and Nucleic Acids by Mass Spectrometry", Current Opinion in Biotech., vol. 6, No. 1, pp. 96–102 (1995).
Liu et al., "Rapid Screening of Genetic Polymorphisms Using Buccal Cell DNA with Detection by Matrix-assisted Laser Desorption/Ionization Mass Spectrometry", Rapid Commun. Mass Spec., vol. 9, pp. 735–743 (1995).
Schöneich et al., "Separation and Analysis of Peptides and Proteins", Anal. Chem., vol. 65, No. 12, 67R–84R (1993).
Shaler et al., "Analysis of Enzymatic DNA Sequencing Reactions by Matrix-assisted Laser Desorption/Ionization Time-of-flight Mass Spectrometry", Rapid Commun. Mass Spec., vol. 9, pp. 942–947 (1995).
Tang et al., "Matrix-assisted Laser Desorption/Ionization Mass Spectrometry of Immobilized Duplex DNA Probes", Nucleic Acids Res., vol. 23, No. 16, pp. 3126–3131 (1995).
Wilding et al., "PCR in a Silicon Microstructure", Clin. Chem., vol. 40, No. 9, pp. 1815–1818 (1994).
Wooley and Mathies, "Ultra-high-speed DNA Fragment Separations Using Microfabricated Capillary Array Electrophoresis Chips", Proc. Natl. Acad. Sci. USA, vol. 91, pp. pp. 11348–11352 (1994).

Primary Examiner—William H. Beisner

[57] ABSTRACT

An integrated nucleic acid sample analysis system for matrix-assisted laser-desorption/ionization time-of-flight mass spectroscopy (MALDI-TOF MS) is described. The integrated system comprises a miniaturized sample preparation compartment interfaced directly with a MALDI-TOF ionization surface for amplifying and/or otherwise chemically manipulating an oligonucleotide analyte and presenting the analyte to a MALDI ionization surface for mass spectrometry analysis. The miniaturized integrated sample handling system disclosed herein finds application in the amplification and analysis of DNA samples for genetic diagnosis and other uses.

19 Claims, 4 Drawing Sheets

INTEGRATED NUCLEIC ACID ANALYSIS SYSTEM FOR MALDI-TOF MS

TECHNICAL FIELD

The present invention relates generally to sample preparation for mass spectroscopy. More particularly, the invention relates to a miniaturized integrated nucleic acid sample handling device interfaced directly with a MALDI-TOF ionization surface. The integrated system disclosed herein finds application in the amplification and analysis of DNA samples for genetic diagnosis and other clinical or forensic uses.

BACKGROUND

The use of DNA analysis in the diagnosis and management of human disease is receiving widespread attention in areas such as infectious disease diagnosis, DNA typing and transplantation, the diagnosis and management of cancer, and in genetic disease diagnosis and screening. See, generally K. J. Skogerboe, "Molecular Biology Techniques", Anal. Chem. 67, 449R–454R (1995).

The ability to detect genetically normal or variant gene sequences in clinical samples generally requires the use of an enzymatic oligonucleotide amplification technique (e.g., the polymerase chain reaction (PCR)) to generate detectable levels of selected regions of DNA for analysis. Sequence analysis requires additional enzymatic or chemical processing steps.

Genetic analysis of human disease involves large-scale detection and screening of clinical DNA samples. Current methods of DNA analysis employ conventional PCR thermal cycling devices and multiple instruments for preparing, separating, and detecting the DNA. Sample preparation is carried out with conventional sample handling devices (test tubes, pipettors, microcentrifuges, concentrators, filtration devices) and involves multiple manual handling steps and transfers. Such procedures are labor-intensive, time-consuming, costly, and susceptible to sample contamination and loss.

The large-scale detection and screening of clinical DNA samples requires automatable, rapid, and cost-effective techniques for sample processing and measurement. These techniques must be sensitive, accurate, and reproducible.

Time-of-flight mass spectrometry (TOF-MS) is one such technique that is potentially capable of being used for DNA-based clinical screening. TOF-MS is the most efficient mass analysis technique in terms of detection sensitivity and readily achieves high mass analysis at good mass accuracy (R. J. Cotter, Anal. Chem. 64(21), 1027 (1992). It is one of the few analysis techniques that combines high sensitivity, selectivity and specificity with speed of analysis. For example, TOF-MS can record a complete mass spectrum on a microsecond timescale.

The technique of matrix-assisted laser desorption/ionization (MALDI) (M. Karas and F. Hillenkamp, Anal. Chem. 60, 2299 (1988) has extended the analytical range of mass spectrometry to oligonucleotides and nucleic acids. See generally, P. Limbach et al, "Characterization of oligonucleotides and nucleic acids by mass spectrometry", In Current Opinion in Biotechnology, 6, 96–102 (1995). The use of MALDI-TOF MS to detect products of a restriction enzyme digest 9 to 622 bp in length with a measurement accuracy of ±2 bp for fragments less than 622 has been reported (Y-H. Liu et at, Rapid Commun. Mass Spec. 9, 735–743 (1995). PCR-DNA fragments from 86 to 426 bp are routinely detected faster than with gel electrophoresis (Y-H. Liu et al, ibid). A 40 base oligonucleotide can be detected with 1-base resolution (T. A. Shaler et at, Rapid Commun. Mass Spec. 9, 942–947 (1995). These reports document the rapid progress that is being made in using mass spectrometry for DNA detection and sequencing, and its application to clinical genetics.

Sample handling is critically important for the successful application of MALDI-TOF MS to clinical genetics. Sample preparation for mass spectroscopy may require the concentration of analyte and/or purification steps to remove contaminants that would otherwise interfere with the accuracy of mass determination and the ion yields for larger oligonucleotides. Purification can be performed either on-probe or off-line. For on-probe purification, analyte is absorbed to a probe surface modified for nonselective (Y-H. Liu et al, Rapid Commun. Mass Spectro. 9, 735–743 (1995) or selective absorption (e.g., an affinity capture surface, see W. T. Hutchens, PCT application/WO 94/28418). A suitably modified probe surface can also be used for analyte concentration. For analytical problems requiring multiple biochemical modifications of oligonucleotide analyte prior to MS detection and measurement (e.g., PCR amplification, restriction enzyme digestions, sequencing reactions), on-probe processing is potentially capable of being used insofar as only a small fraction of matrix-embedded analyte is actually desorbed during MALDI. However, this procedure increases the likelihood of contamination or loss of the sample during the repetitive withdrawal and reinsertion of the probe into the source of the mass spectrometer and during the washing away of matrix prior to biochemical modification of the analyte. Off-line purification and concentration of analyte is more widely used, but requires multiple manual transfers, and mixing and concentration steps, which are labor-intensive and time-consuming and increase the risk of sample loss.

The paucity of efficient sample preparation and handling techniques remains a serious limitation for routine use of mass spectroscopy for nucleic acid analysis. Since mass measurements can be performed in a fraction of the time required for sample preparation and handling, sample handling is the rate limiting step in the analytical process. Recently, DNA sample preparation technologies have been successfully reduced to miniaturized formats. See, e.g., P. Wilding et al, Clin. Chem. 40, 1815–1818 (1994) (PCR microchip); A. T. Woolley and R. A. Mathies, Proc. Natl. Acad. Sci. 91, 11348–11352 (1994) (capillary array electrophoresis microchip); M. Eggers and D. Ehrlich, Hematol. Pathol. 9, 1–15 (1995) (microfabricated devices for gene-based diagnostics). Emerging technologies for miniaturizing detector devices have also been reported (Cambridge Healthtech Institute Conference on Microfabrication Technology, Sep. 28–29, 1995, San Francisco, Calif.). The integration of a miniaturized sample handler with a sample presentation device would have the advantage of increased speed of analysis, decreased sample size and reagent consumption, decreased sample loss and contamination, and increased detection efficiency and accuracy.

Accordingly, there has remained a need for an integrated nucleic acid analysis system for MALDI-TOF MS which is designed to avoid the inherent shortcomings of conventional sample handling techniques while retaining the advantages of mass spectrometry detection and measurement.

SUMMARY OF THE INVENTION

To address the above-mentioned need in the art, the invention disclosed and claimed herein provides an integrated nucleic acid analysis system for MALDI-TOF MS in a thin film support, wherein the system is comprised of a miniaturized sample handler integrated with a MALDI ionization surface for detection and measurement of oligonucleotide analytes in a time-of-flight mass spectrometer.

It is an object of the present invention to provide an automatable device for improved sample handling prior to mass spectrometric analysis. A miniaturized system according to the present invention is capable of performing complex sample handling, separation, and presentation of oligonucleotide analytes for mass spectrometry with speed and precision without the need for significant manual manipulation and interaction.

It is yet another object of the present invention to handle small amounts of sample with minimal sample loss. A miniaturized sample preparation compartment having automatable means for separating, biochemically manipulating and moving oligonucleotide analytes from point to point within the compartment greatly reduces the likelihood of sample loss.

It is a related object of the present invention to increase the sensitivity and selectivity of analyte measurement by providing capture regions within the sample handling compartment for concentrating an oligonucleotide present in low concentration in the sample and for removing potentially interfering molecules and ions from the analyte sample prior to mass spectrometry, thereby increasing the signal and decreasing the noise in the mass spectrum.

It is a further related object of the present invention to increase selectivity and sensitivity of analyte measurement by providing means to perform rapid cycle DNA amplification on an oligonucleotide sample thereby to amplify selected DNA regions to detectable levels for mass spectrometry.

It is yet a further related object of the present invention to provide one or more oligonucleotide-processing reaction zones with immobilized enzymes. The use of immobilized enzymes in the present invention is intended to provide increased enzyme stability with improved reaction kinetics, decreased loss of enzyme from non-specific adsorption to surfaces, and decreased contamination of reaction zones with undesired enzymes.

It is yet a further related object of the present invention to enable the performance of multiple concurrent or consecutive analyses within the same experiment with on-line monitoring capability. In one preferred embodiment of the present invention, it is contemplated to provide a plurality of MALDI ionization surfaces within the sample preparation which can be reversibly sealed during mass spectrometry. An alternative preferred embodiment contemplates placement of the MALDI ionization surface in a rotatable comb device which alternates between sample collection and sample presentation functions.

It is yet a further related object of the present invention to reduce the cost of analyzing oligonucleotides by mass spectroscopy by constructing the analysis system as a single disposable unit. For large-scale diagnostic screening of genetic samples, the disposable feature will eliminate cross-contamination of samples and reduce false positive results.

BRIEF DESCRIPTION OF THE FIGURES

FIG 3A: plan view of the upper surface showing particular features of the sample preparation compartment; FIG. 3B: plan view of the upper surface showing placement of apertures.

DETAILED DESCRIPTION OF THE INVENTION

Figure 1:
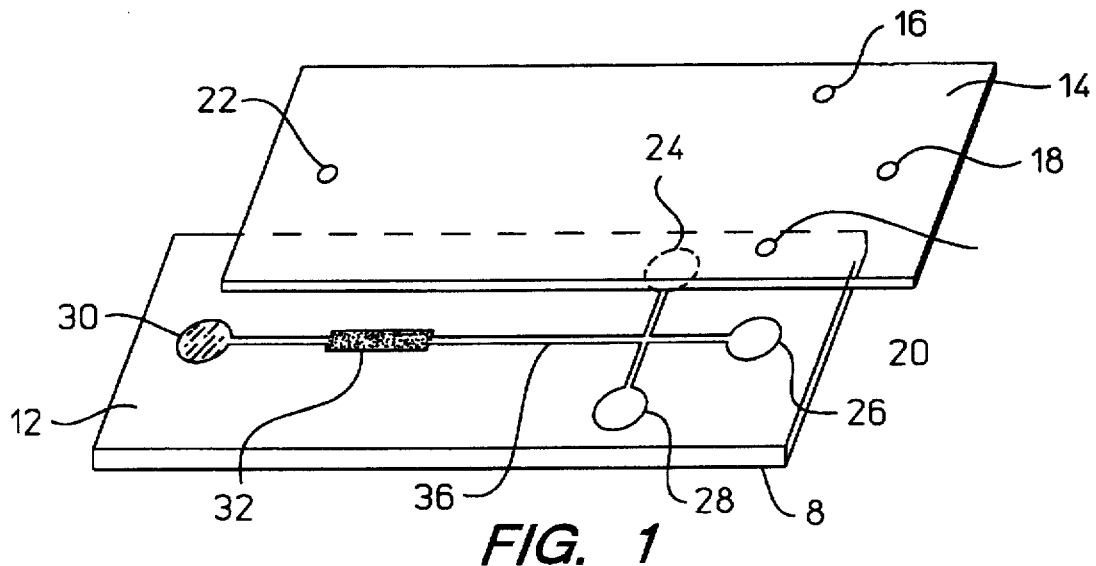
FIG. 1 is an exploded view of a sample handling system integrated with a MALDI ionization surface.

Before the invention is described in detail, it is to be understood that this invention is not limited to the particular component parts of the device described or process steps of the methods described, as such devices and methods may vary. It is also to be understood that the terminology used herein is for purposes of describing particular embodiments only, and is not intended to be limiting. As used in the specification and the appended claims, the singular forms "a", "an", and "the" include plural referents unless the context clearly indicates otherwise. Thus, for example, reference to "an analyte" includes mixtures of analytes, reference to "a MALDI ionization surface" includes two or more such ionization surfaces, reference to "a microchannel" includes more than one such component, and the like.

In this specification and in the claims which follow, reference will be made to a number of terms which shall be defined to have the following meanings:

The term "thin film support" is used herein to refer to a substantially planar manifold made of a non-conducting material that includes a microchannel and other necessary components of a miniaturized sample preparation compartment, an interface to non-consumable parts, and an ionization surface for MALDI-TOF MS. Such a miniaturized device may be formed from a variety of materials (e.g., silicon, glass, low cost polymers) by techniques that are well-known in the art (e.g., micromachining, chemical etching, laser ablation, and the like). Portions of the device may be fabricated from composite materials. For example, a thermally insulated reaction zone may be formed from bonded layers of materials having different thermal conductivities. Established techniques exist for micromachining planar materials such as silicon and provide a useful and well-accepted approach to miniaturization. Examples of the use of such micromachining techniques to produce miniaturized separation devices on silicon or borosilicate glass chips can be found in U.S. Pat. No. 5,194,133 to Clark et al; U.S. Pat. No. 5,132,012 to Miura et al, U.S. Pat. No. 4,908,112 to Pace; and in U.S. Pat. No. 4,891,120 to Sethi et al.

The term "sample preparation compartment" is used herein to refer to a region of the support in which sample handling is carried out. Sample handling includes the entire range of operations capable of being performed on the sample from its introduction into the compartment until its removal for analysis or use. Such operations may include but are not limited to: concentrating an oligonucleotide analyte from a dilute solution (e.g. by selective absorption to a chemically-modified surface); separating an oligonucleotide analyte from potentially interfering molecules and ions (e.g., by chromatographic and/or electrophoretic procedures); performing ion exchange or buffer exchange on an oligonucleotide analyte-containing fluid; chemically manipulating an oligonucleotide analyte (e.g., by amplification, nuclease digestion, addition or removal of nucleotides, covalent modifications of nucleotides, oligonucleotide hybridization and denaturation, and the like).

The sample preparation compartment frequently will include one or more access ports for introducing materials into, and withdrawing materials from the compartment (e.g., introduction of sample and reagents, flushing the compartment or a region thereof with fluid from an external reservoir).

The sample preparation compartment will also include one or more "reaction zones" for chemical manipulation of the oligonucleotide analyte, as described above. These reaction zones are regions where reactants and catalysts are spatially localized for a sufficient time to carry out the intended reaction. It is useful and often essential to maintain a uniform and constant temperature within a reaction zone. Thus it is contemplated that the sample preparation compartment will include temperature controlling devices (e.g., sensors, thermocouples, heaters, and adequate thermal insulation surrounding reaction zones to prevent unintended cross-heating of other regions of the compartment. In particular, where it is desired to perform PCR (polymerization chain reaction)-mediated amplification rather than isothermal amplification, uniform temperature profiles, rapid temperature cycling and precise temperature control is essential. A computer-controlled Peltier heater-cooler is useful for this purpose. See, e.g., P. Wilding, M. A. Shoffner, and L. J. Kricka, *"PCR in a Silicon Microstructure"*, Clin. Chem. 40 (9), 1815–1818 (1994). Given the present state of the art disclosed by M. A. Northrup, M. A. Burns and others (Cambridge Healthtech Institute Conference on Microfabrication Technology, Sep. 28–29, 1995, San Francisco, Calif.), extremely rapid and accurate thermal cycling can be achieved (e.g., using a 35 V, 0.5 amp device, it is possible to achieve a 30° C. per second ramp rate). Adequate insulation can be achieved by proper design of the heating chamber and the use of appropriate materials known to one skilled in the art (e.g. multilayered silicon and silicon nitride).

The term "oligonucleotide" is used herein to refer to naturally occurring or synthetic double-and single-stranded DNA molecules and double- and single-stranded RNA molecules.

The terms "analyte", "sample analyte" and "oligonucleotide analyte" are used interchangeably herein to refer to one or more oligonucleotide species whose mass is to be measured by the technique of MALDI-TOF MS. Prior to analysis, the analyte may require amplification, covalent modification, concentration or separation from potentially interfering molecules and ions in the sample preparation compartment. The term "analysis" is used herein to refer to the application of MALDI-TOF MS for detection and structure elucidation of an oligonucleotide analyte.

An oligonucleotide analyte can be obtained from a variety of natural sources, e.g., biological fluids or tissue extracts, genetic DNA or RNA from microorganisms, viruses, recombinant cells, food stuffs, and environmental materials, or can be originated by chemical synthesis (e.g., sequences prepared by combinatorial synthesis), and prepared for use in the present invention by a variety of means, e.g., protease digestions, chaotropic salt extractions, organic extractions, and the like. It is contemplated that means for handling unprocessed samples can be incorporated into the present invention by one skilled in the art without undue experimentation.

The terms "analyte-binding partner" and "oligonucleotide-binding partner" are used herein to refer to molecules that may recognize general structural features (e.g., single or double strandedness) of the "target analyte" (i.e., the oligonucleotide intended to be bound to the binding partner). Alternatively, the binding partner may recognize specific nucleotide sequences in the target analyte. Binding partners may include oligonucleotide binding proteins and antibodies as well as oligonucleotides or peptide nucleic acids containing homologous base pair sequences for hydrogen bonding to the target analyte. Any of the aforementioned types of "analyte-binding partners" can be used in the present invention if they possess a sufficiently high binding affinity and selectivity for the target analyte to permit the invention to be practiced.

The term "MALDI" is used herein to refer to Matrix-Assisted Laser Desorption/Ionization, a process wherein analyte is embedded in a solid or crystalline "matrix" of light-absorbing molecules (e.g., nicotinic, sinapinic, or 3-hydroxypicolinic acid), then desorbed by laser irradiation and ionized from the solid phase into the gaseous or vapor phase, and accelerated as intact molecular ions towards a detector. The "matrix" is typically a small organic acid mixed in solution with the analyte in a 10,000:1 molar ratio of matrix/analyte. The matrix solution can be adjusted to neutral pH before use.

The term "MALDI-TOF MS" is used herein to refer to Matrix-Assisted Laser Desorption/Ionization Time-of-Flight mass spectrometry.

The term "MALDI ionization surface" is used herein to refer to a surface for presentation of matrix-embedded analyte into a mass spectrometer for MALDI. In general, the terms "probe" or "probe element" are used interchangeably to refer to a device for presenting analyte into a mass spectrometer for irradiation and desorption.

Metals such as gold, copper and stainless steel are typically used to form MALDI ionization surfaces. However, other commercially-available inert materials (e.g., glass, silica, nylon and other synthetic polymers, agarose and other carbohydrate polymers, and plastics) can be used where it is desired to use the surface to actively capture an analyte or as a reaction zone for chemical modification of the analyte. The use of Nafion and nitrocellulose-coated MALDI probes for on-probe removal of salts from PCR-amplified gene sequences is reported by Y-H. Liu et al, Rapid Commun. Mass Spec. 9:735–743 (1995). Tang et al have reported the MALDI analysis of short DNA duplex probes with one strand immobilized on a solid support (streptavidin-coated magnetic beads or controlled pore glass beads) (K. Tang et al, Nucleic Acids Res. 23, 3126–3131, (1995)).

The term "capture region" is used herein to refer to a region or regions within the sample presentation compartment wherein sample handling functions that require immobilization of the analyte can be performed (e.g., concentration of analyte from a dilute solution, removal of potentially interfering molecules and ions initially present in the sample or introduced during analyte handling, buffer exchange, and the like).

Capture regions may be formed by well-known methods for attaching biological molecules to solid supports. See generally, *Affinity Techniques. Enzyme Purification: Part B. Methods in Enzymology*, Vol. 34, ed. W. B. Jakoby, M. Wilchek, Acad. Press, N.Y. (1974) and *Immobilized Biochemicals and Affinity Chromatography, Advances in Experimental Medicine and Biology*, Vol. 42, ed. R. Dunlap, Plenum Press, N.Y. (1974), which are incorporated herein by reference. For example, the surface of a bead, particle or planar support can be treated with a bifunctional cross-linking reagent (i.e. a cross-linking reagent having the same or different chemical reactivities on each end of a molecular linker) to attach one end of the reagent to reactive groups on the surface, and the opposite end to a biological molecule. The cross linker is preferably of sufficient length to permit attached biological molecules to interact freely with compounds in solution. Crosslinking groups may be attached to the surface by siloxane bonds using organosilanes such as such as 3-glycidoxypropyltrimethoxysilane ("GOPS"), 3-aminopropyltriethoxysilane (APS), and the like, which have well-understood chemistries. For immobilization of oligonucleotide probes to $SiO_2$ surfaces using epoxy-silane and amine-modified oligonucleotide probes, see Eggers et al, BioTechniques 17:516–524 (1994). Another preferred method of immobilizing biological molecules to surfaces is to covalently attach avidin or streptavidin protein to the surface, and subsequently to react the surface with an analyte binding partner that has been covalently bound to biotin or a biotin analog. Avidin and streptavidin bind biotin noncovalently but with very high affinity (the $K_a$ is approximately $10^{15}M^{-1}$). See Green, "Avidin" in Advances in Protein Chemistry, Academic Press, vol. 29, 105 (1975). Biotinylated oligonucleotides can be prepared as described in the literature. See e.g., Bayer et al, Methods of Biochemical Analysis, Vol. 26 (D. Click, ed.), 1–45 (1980), and Current Protocols in Molecular Biology, Supplement 20 (John Wiley & Sons, Inc.), which are incorporated herein by reference.

According to the practice of the present invention, a capture region may be formed in any microstructure surface in the sample preparation compartment by linking an analyte binding partner directly to the surface, and on MALDI ionization surfaces integrated with the preparation compartment. Alternatively, a capture region may be formed on the surfaces of beads which can be chemically attached to the surface of the support, or magnetically attached by using magnetically responsive beads and applying a magnetic field to anchor the beads to the desired region of the support. Magnetically responsive beads and particles are well-known in the art and are commercially available from, for example, Dynal®, Inc. (Lake Success, N.Y.) and Bangs Laboratories, Inc. (Carmel, Ind.).

In addition to affinity capture methods, which are preferred for the practice of the present invention, analyte capture can be effectuated by hydrophobic or charge interactions, or by chelational mechanisms as indicated above.

A captured oligonucleotide analyte may be released into solution by various methods known in the art to denature oligonucleotide duplexes or to dissociate high affinity oligonucleotide-protein binding complexes by disrupting H-bonds and/or by affecting polar or nonpolar interactions (e.g., changing temperature, pH, solvent polarity, using chaotropic salts, localized heating with laser irradiation, and the like). Changes in electric field strength can be used to disrupt electrostatically-mediated binding interactions between captured oligonucleotides and their binding partners. An analyte captured on a magnetically responsive particle can be mobilized by altering the magnetic field strength. In practicing this invention, it is contemplated that heating of the MALDI surface may be used to facilitate release of an oligonucleotide from a capture region localized therein.

The term "reaction zone" is used herein to refer to a region in the sample preparation compartment containing an immobilized catalyst (e.g., an enzyme, catalytic antibody, a catalytic surface formed by molecular imprinting, a ribozyme, and the like). Immobilization of catalysts within a reaction zone can be accomplished by any well-known art method that provides stable linkages and sufficient catalytic activity to practice the present invention (described above under "capture region").

The reaction zone may be formed within a microchannel, a well, or another microstructure in the sample preparation compartment, or on a MALDI ionization surface. A plurality of reaction zones may be provided within the same sample preparation compartment for simultaneously carrying out a single reaction under different reaction conditions (e.g., for optimizing a PCR reaction) or for successive chemical manipulations of an oligonucleotide analyte (e.g., restriction enzyme digestions, sequencing reactions), or for simultaneously carrying out reactions with multiple analyte species, or any combination thereof.

Typically, the reaction zones of this invention will be individually temperature-controlled, and will be contiguous with microchannels. It is contemplated that microvalves and/or valveless pumps will be appropriately positioned in the sample preparation compartment to direct the flow of analyte to appropriate reaction zones. Means for moving the analyte from one point to another in the sample preparation compartment can be used to mix soluble reactants prior or subsequent to entry into a reaction zone (e.g., electroosmosis, electrokinesis, hydrodynamic flow or any other technique that is known to be suitable for use in miniaturized sample handling devices).

The term "surface treatment" is used herein to refer to the preparation or modification of the microstructure surfaces of the sample preparation chamber for biocompatibility and for prevention of non_specific adsorption of biomolecules. Such treatments include coating surfaces with proteins, non-reactive silanes, teflons and other polymers well-known in the art to reduce or eliminate non-specific adsorption of biomolecules to the surface during sample handling (See, e.g., C. Schöneich et al, Anal. Chem. 65: 67R–84R (1993) for a detailed description of procedures that have been used in the art).

The term "amplification" is used herein to refer to any in vitro method for increasing the copy number of a target nucleic acid sequence. Amplification techniques include those requiring temperature cycling (e.g., the polymerase chain reaction (PCR), the ligase chain reaction (LCR), and the polymerase/ligase chain reaction (PLCR)) and those which can be performed under isothermal conditions (e.g., strand displacement amplification (SDA), nucleic acid sequence based amplification (NASBA), and self-sustained sequence replication (3 SR)).

The polymerase chain reaction (PCR) technique, which was the first amplification technique to be developed and the technique with the broadest applications for use of the present invention for genetic diagnosis in a clinical laboratory setting, involves denaturation of a DNA—DNA duplex containing the target oligonucleotide sequence for amplification, at a temperature of about 94° C.; annealing of primers to each of the template strands at positions flanking the target oligonucleotide sequence, at about 55° C. or 60° C.; and primer extension with a thermophilic DNA polymerase at about 72° C. This reaction sequence is repeated for about 30 cycles with extension products from each cycle serving as target in the next cycle, thereby producing exponential amplification.

The term "transparent" as used herein refers to the ability of a material to transmit light of different wavelengths, which may be measured as the percent of radiation which penetrates a distance of 1 meter. For example, in the practice of the present invention, the upper surface of the sample preparation compartment is preferably transparent to permit sample handling to be observed microscopically, if desired, and to facilitate laser irradiation of the sample preparation compartment, when necessary.

"Optional" or "optionally" means that the subsequently described feature or structure may or may not be present in the analysis system or that the subsequently described event or circumstance may or may not occur, and that the description includes instances where said feature or structure is present and instances where the feature or structure is absent, or instances where the event or circumstance occurs and instances where it does not. For example, the phrase "said capture region is optionally provided with access ports" means that the capture region may or may not be provided with access ports and that the description includes both circumstances where access ports are present and absent.

The term "vacuum gate" as used herein refers to an opening into the vacuum chamber of a mass spectrometer for insertion of the MALDI ionization surface therein.

Unless otherwise indicated, the practice of the present invention will employ conventional techniques of molecular biology and recombinant DNA technology which are within the skill of the art. These techniques are fully explained in the literature. See, e.g., *Current Protocols in Molecular Biology* (John Wiley & Sons, Inc.), and G. H. Keller and M. M. Manak, *DNA Probes*, 2nd Ed., (Stockton Press, 1993), which are incorporated herein by reference.

According to the invention, an integrated nucleic acid analysis system for MALDI-TOF MS can be constructed in a single low cost consumable unit formed predominantly from a non-conducting material such as glass, silicon, or a low-cost plastic polymer. The unit can include microchannels, reaction zones for carrying out chemical and enzymatic reactions, interfaces to non-consumable parts, and an ionization surface for MALDI-TOF MS. Using emerging technologies found in micromachining and nanotechnology, low cost thin film supports can be etched with microchannels, mixing chambers, wells, and valves to allow an oligonucleotide analyte to be introduced, moved through a series of chemical manipulations which are spatially and therefore temporally separated, and deposited on a MALDI ionization surface interfaced with a mass spectrometer. The entire sequence of steps from sample introduction to sample detection is capable of being automated.

Figure 2A:
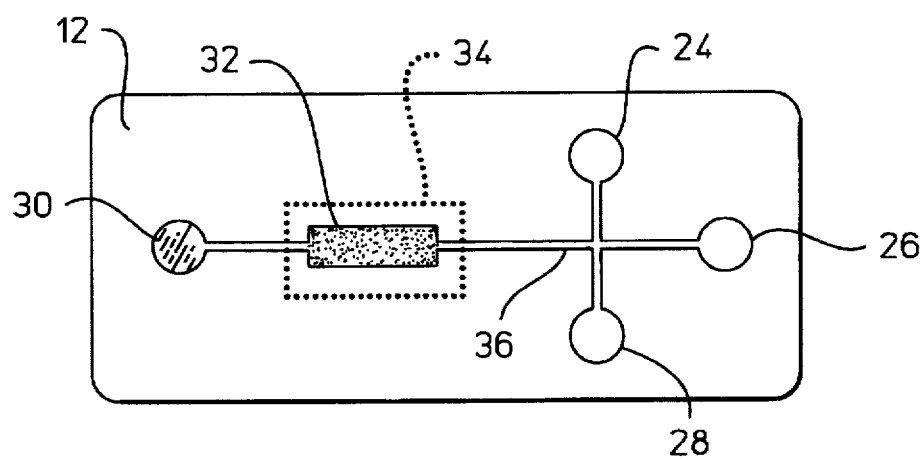
FIG. 2A is a plan view of the upper surface of the integrated sample handling system of FIG. 1.

A particular embodiment of the invention in its simplest form is shown in FIGS. 1 and 2. FIG. 1 is an exploded view of an integrated analysis system showing the thin film support with components of the sample preparation compartment defined in the upper surface (12) of the support. The upper surface is optionally enclosed by a cover (14) that can be fixably aligned over the support surface to form a liquid-tight sample preparation compartment by using pressure sealing techniques, by using external means to urge the pieces together (e.g., clips or tension springs), or by using adhesives well known in the art of polymer bonding. The cover is preferably formed from a transparent material to permit microscopic observation of sample introduction and handling steps and for laser irradiation. The cover includes apertures (16, 18, 20) spatially aligned with wells (24, 26, and 28 in FIG. 2A) and an aperture (22) aligned with a MALDI ionization surface (30) in the sample preparation compartment to form access ports when the cover is attached to the support. The MALDI ionization surface (30) is preferably made of a typical MALDI surface material such as gold, but can be made of other well-known materials if necessary, as described in detail above. A reaction zone (32) is positioned between the MALDI ionization surface and the sample wells. The reaction zone is provided with means for immobilizing enzymes to catalyze the synthesis, digestion, fragmentation, covalent modification, reverse transcription and other reactions of nucleic acid and oligonucleotide substrates, and means for carrying out these reactions in a temperature-controlled environment (34). It is contemplated that catalytic antibodies, ribozymes, and other biocatalysts can be used in the present invention. Connecting the wells, reaction zone and MALDI ionization surface are microchannels. One such microchannel is indicated at 36. It will be readily appreciated that the representation of the microchannel (36) in a generally extended form is for illustrative purposes and is not intended to limit the shape or geometry of microchannels of this invention. The present invention also contemplates a sample preparation compartment having a plurality of microchannels. Further, the spatial arrangement of wells, reaction zones and ionization surfaces on the support is determined in part by the analytical procedures and their requirements and is not intended to be limited to any particular arrangement shown in these Figures.

Figure 2B:
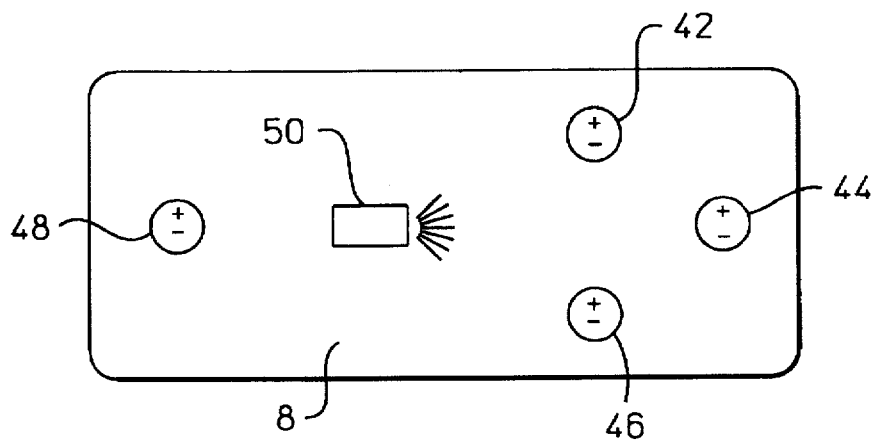
FIG. 2B is a plan view of the exterior lower surface of the integrated sample handling system of FIG. 1.

FIG. 2B is a plan view of the exterior lower surface (8) of the thin film support showing electrical connections (42, 44, 46, 48) and a peltier surface (50) positioned to provide temperature control to the reaction zone. In this embodiment of the invention, it is intended that the thin film support is placed on a preparation station which would provide electrical connections to each of the wells and which could provide temperature control via the peltier surface (50).

Further, as described in detail above, it is contemplated to apply localized magnetic fields to selected regions of the thin film support containing magnetically-responsive particles as a means of moving the particles from one region of the sample preparation compartment to another.

Accordingly, in the practice of the invention, a small volume of oligonucleotide analyte (e.g., circa 1 µL or less) is injected into a sample well and is automatically moved from the well to the microchannel. For the purpose of this discussion, we will assume that analytes and reagents are injected into wells and moved from point to point by electromotive forces acting electrophoretically on charged molecules and electroosmotically on uncharged molecules. Simultaneously, reagents are injected into a second well and are moved from the well to the microchannel where they mix with the analyte. The reaction mixture is moved into the reaction zone and brought into contact with an immobilized enzyme contained therein. The reaction zone temperature is automatically measured and adjusted to a desired reaction temperature where it is held constant for a fixed time (assuming isothermal reaction conditions). The oligonucleotide analyte is allowed to react under static conditions by turning off the flow or can be dynamically mixed in the reaction region by oscillating the electrical potential or magnetic field or pressure difference across the reaction zone to cause the flow to go back and forth. The reacted oligonucleotide analyte is moved onto the MALDI ionization surface, mixed with matrix, dried, and the support is transferred to the MALDI-TOF MS vacuum system for commencement of the MALDI experiment. Following the measurement, the support is removed and discarded.

The immobilization of enzyme within a reaction zone offers several important advantages over the use of enzymes in solution, including increased enzyme stability; decreased loss of enzyme by non-specific adsorption to surfaces; decreased or negligible carryover of enzyme to other reaction zones; and the ability to achieve a high concentration of enzyme for catalytic reaction with a very small concentration of substrate to improve kinetic rates of dilute sample solutions without increasing the molar concentration of enzyme in solution, thereby minimizing the contamination of the analyte with enzyme impurities.

The advantage of integrating the sample preparation compartment with the MALDI ionization surface is to allow automated chemical manipulation of analytical samples prior to analysis by MALDI-TOF MS without manual sample handling, thus reducing contamination and sample loss while allowing specific chemical pretreatment prior to MALDI analysis to enhance the selectivity, sensitivity and/ or reproducibility of the measurements. This feature will be of particular importance if the full sensitivity of MALDI-TOF is to be achieved. With particular reference to the present invention, the integration of a miniaturized nucleic acid analysis system, having the capability of amplifying small amounts of oligonucleotide analytes, with MALDI-TOF MS is intended to provide a highly sensitive, accurate, rapid, and reproducible technique for detecting and elucidating the structure of oligonucleotides present in relatively small quantities in clinical and forensic samples. The sensitivity of detection (between $10^{-12}$ to $10^{-15}$ moles of oligonucleotide deposited on a MALDI ionization surface) means that an oligonucleotide analyte need not be amplified to the same extent as is required for other analytical techniques, while the speed of measurement (on the order of a few minutes) should facilitate the performance of multiple mass determinations in a single experiment. The use of disposable probes is intended to minimize sample contamination.

Figure 3A:
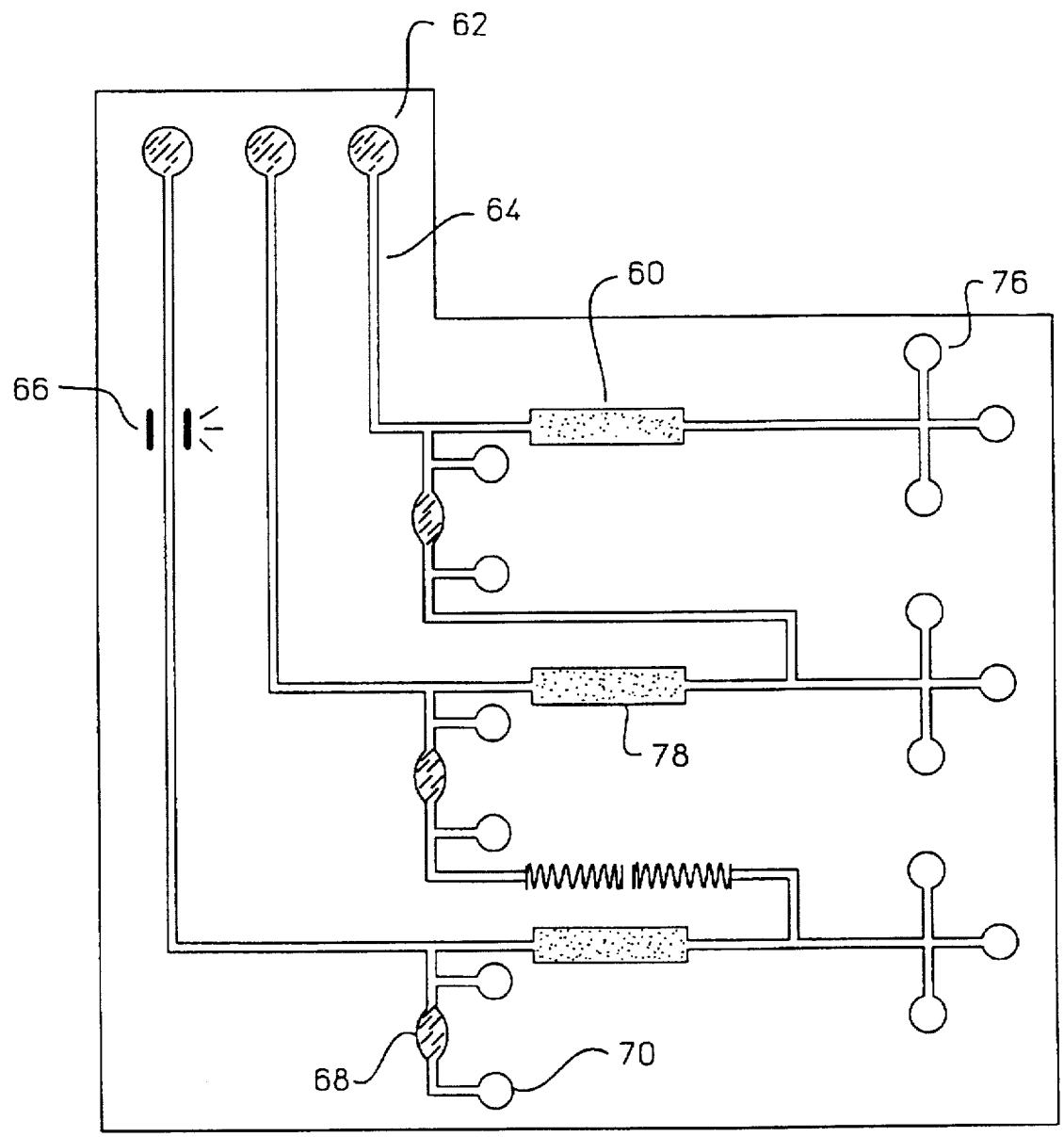
FIGS. 3A and 3B show a preferred embodiment of the integrated sample handling system of FIG. 1.
Figure 3B:
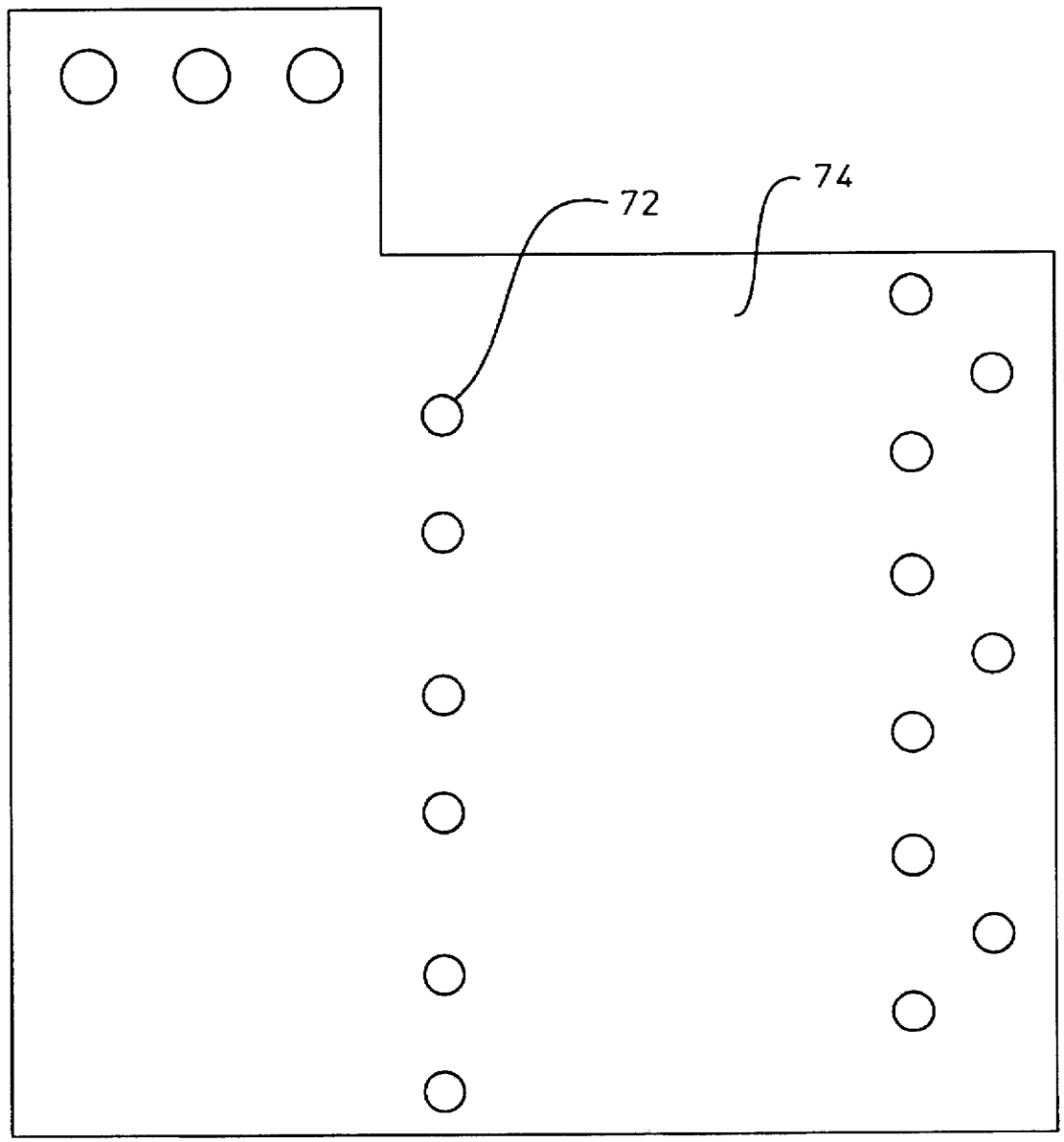

Referring now to FIG. 3A, in a preferred embodiment of the invention, multiple reaction zones (60) are serially arranged on the support surface. Each zone can contain the same or a different immobilized enzyme. A plurality of MALDI ionization surfaces (generally indicated at 62) is included within the sample preparation compartment positioned distal to the reaction zones. The connecting fluid-filled microchannels (64) are optionally equipped with reversible sealing means (66) (e.g., a thermally-expandible metal with localized heating means), for sealing the channels when the MALDI surfaces are interfaced with the vacuum gate of the mass spectrometer. Capture regions (68) are interposed between successive reaction zones. As described above in detail, these regions are adapted chemically or magnetically to selectively retain oligonucleotide analyte after processing. This feature enables contaminants introduced during a chemical reaction to be removed by washing the analyte prior to measurement in the mass spectrometer, or prior to carrying out additional reactions on the analyte, or prior to collection of the analyte for other uses. Thus, each capture region is optionally associated with wells (70) and access ports (72, FIG. 3B) in the thin film support cover (74, FIG. 3B). The directional movement of analyte from a reaction zone to a capture region, and from a capture region to a MALDI ionization surface, or alternatively, from a capture region to the next reaction zone in the series, is controlled by microvalves (not shown). Referring to FIG. 3A, a plurality of wells (76) interconnected by microchannels feed into each reaction zone.

As an example of consecutive processing of an analyte, an analyte is first reacted in zone 60, then moved into its corresponding capture region for washing, release, and movement to zone 78. Following reaction in zone 78, the analyte is moved to the next capture region, and so on, until the desired sequence of reactions has been completed. After a final capture and wash, the analyte is released for movement to its corresponding MALDI ionization surface (62) or to a collection well (indicated generally at 70).

As an example of concurrent processing of one or more analytes through a single reaction step, the individual reaction zones can be isolated from one another by closing off the connecting microchannel as shown. Sample analyte and reagents can be injected into the microchannel for any given zone as previously described for the embodiment shown in FIGS. 1 and 2.

Figure 4A:
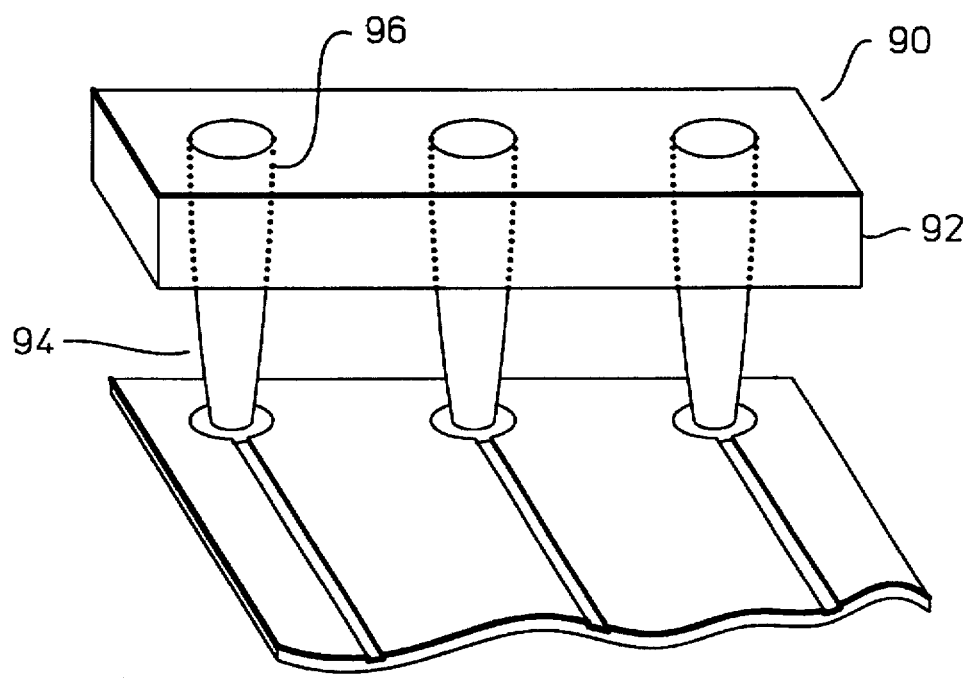
FIGS. 4A and 4B show a comb device containing a plurality of MALDI ionization surfaces in the handle (FIG. 3A) and a comb device containing a plurality of toothwicks comprising MALDI ionization surfaces with capture regions (FIG. 3B).
Figure 4B:
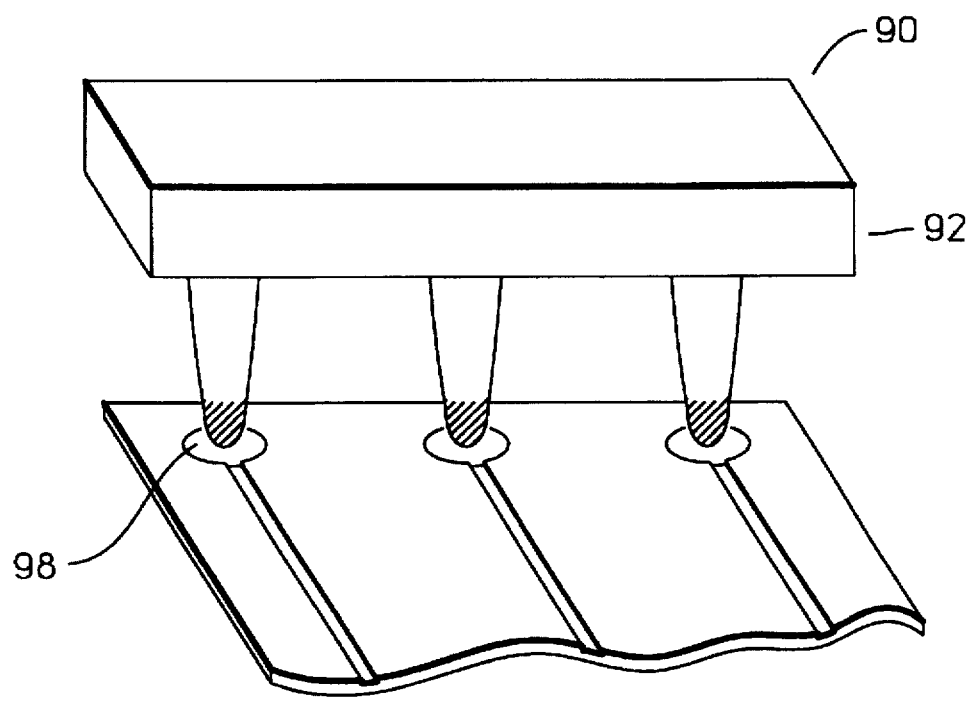

An alternative preferred embodiment of the invention is shown in FIGS. 4A and 4B. Here the MALDI ionization surface is contained in a rotatable comb device (shown generally at 90) having a handle (92) and teeth. The teeth can be hollow tube-like structures (94) that extend upwardly to form MALDI ionization surfaces (96) in the handle, or the teeth can be solid toothwicks with analyte capture regions (FIG. 4B; (98)). When the comb is rotated to a first position, the tips of the teeth are brought into contact with fluid analyte-containing wells in the sample preparation compartment serving thereby to draw fluid analyte into the tube-like teeth by capillary action. Analyte is mixed with matrix in the handle portion of the tube and is subsequently dried onto the ionization surface (96). Alternatively, the analyte is actively captured on toothwick capture regions (98). Upon rotation of the comb to a second position, the MALDI ionization surface, located either in the comb handle (FIG. 4A; 96) or comprising the toothwick capture region (FIG. 4B; 98) is aligned with the vacuum gate of a mass spectrometer for insertion thereto. Matrix is deposited on the capture surface of the toothwicks and allowed to dry prior to insertion of the toothwick into the mass spectrometer vacuum gate.

It is to be understood that while the invention has been described in conjunction with the preferred specific embodiments thereof, the description above is intended to illustrate and not limit the scope of the invention. Other aspects, advantages and modifications within the scope of the invention will be apparent to those skilled in the art to which the invention pertains.

The following example is put forth so as to provide those of ordinary skill in the art with a complete disclosure and description of how to use the method of the invention, and is not intended to limit the scope of what the inventors regard as their invention. Efforts have been made to ensure accuracy with respect to numbers (e.g., amounts, temperature, etc.), but allowances should be made for some errors and deviations. Unless indicated otherwise, parts are parts by weight, temperature is in ° C. and pressure is at or near atmospheric.

EXAMPLE

PCR Amplification of HLA $DQ_\alpha$ alleles

The following flanking oligonucleotide primers are designed for use in amplifying each of the corresponding $DQ_\alpha$ subtypes listed below:

| | |
|---|---|
| $DQ^\alpha 1.1$ | a) 5' CAG TCT CCT TCC TCT CCA 3' |
| | b) 5' TGG AGG TTT TGA CCC GCA 3' |
| $DQ^\alpha 1.2$ | a) 5' GTA GAA CTG CTC ATC TCC 3' |
| | b) 5' TGG AGG TTT TGA CCC GCA 3' |
| $DQ^\alpha 1.3$ | a) 5' ATT CAT GGG TAT ACT GGC 3' |
| | b) 5' TGG AGA AGA AGG AGA CTG 3' |
| $DQ^\alpha 2$ | a) 5' AGA GGC AAC TTC CAG GCA 3' |

-continued

| | |
|---|---|
| | b) 5' AGA TTT GAC CCG CAA TTT 3' |
| DQα3 | a) 5' TGG CTG TAC TGC CCA GAG 3' |
| | b) 5' GTT CCG CAC ATT TAG AAG 3' |
| DQα4.1 | a) 5' TCC CCA GGT CCA CGT AGA ACT GCT 3' |
| | b) 5' GTG TTT GCC TGT TCT CAG 3' |
| DQα4.2 | a) 5' ACT CCT CAT CTC CAT CAA 3' |
| | b) 5' GTG TTT GCC TGT TCT CAG 3' |
| DQα4.3 | a) 5' TGG GTA TAC TGG CCA GAG 3' |
| | b) 5' GTG TTT GCC TGT TCT CAG 3' |

Human DNA is prepared from 10–50 μL of whole blood by lysis in 50 mM Tris-OH (pH 8.0), 50 mM EDTA, 1% SDS, 100 mM NaCl, 1% 2-mercaptoethanol, and digestion with proteinase 200 μg/ml final concentration) and RNAse A (100 μg/ml final concentration). The DNA contained in the lysate is deproteinized by phenol extraction, precipitated, and resuspended in 100 μl 1×TE buffer (10 mM Tris, pH 8.0, 1 mM EDTA).

To amplify the extracted DNA, 2–3 μl are added to the amplification reaction mixture containing reaction buffer (50 mM KCl, 10 mM Tris-OH, pH 8.4 at 22° C., 2.5 mM MgCl$_2$ and 0.01% gelatin), piers (20 pmoles), and deoxynucleotide triphosphates (dNTPs) (20 nmoles). The reaction mixture is introduced into the sample preparation region and moved to a reaction zone containing immobilized Taq polymerase (2.5 units). The final volume of the amplification reaction is 10 μL to 20 μL. The temperature of the reaction zone is raised to 95° C. to denature the target DNA, then rapidly cycled for a total of 25–40 cycles to amplify the DNA. Typically, the temperature-cycling profile will involve denaturation at 95° C., 1 minute, annealing at 55–60° C., 30 seconds, and extension at 72° C., 1 minute.

At the completion of amplification, the amplified DNA is moved from the reaction zone into the microchannel leading to the MALDI ionization surface. A portion of the DNA is diverted to the first capture region. The remainder is moved to the MALDI ionization surface. The microchannel connecting the MALDI surface to the first reaction zone is sealed, the MALDI matrix is added and dried, and the support is transferred to the vacuum gate of the mass spectrometer for detection.

After mass measurements are made, the support is removed from the mass spectrometer, and the captured DNA is ready for further analysis and characterization.

What is claimed is:

1. An integrated nucleic acid analysis system for a MALDI-TOF mass spectrometer comprising a thin film support having:
   (a) a sample preparation compartment for receiving and handling an oligonucleotide analyte, said compartment including a well for receiving liquid substances for sample preparation, a temperature-controlled reaction zone comprising means for immobilizing a catalyst thereto for chemically manipulating an oligonucleotide analyte therein, and a microchannel interconnecting said well and said reaction zone;
   (b) automatable means for moving an oligonucleotide analyte and fluids within said compartment;
   (c) automatable means for controlling the temperature of said compartment over a range of about 10° C. to about 100° C.; and
   (d) a MALDI ionization surface in communication with said sample preparation compartment through said microchannel.

2. The integrated nucleic acid analysis system of claim 1, wherein said thin film support further includes a port in fluid communication with said microchannel for inputting materials to and withdrawing materials from said sample preparation compartment.

3. The integrated nucleic acid analysis system of claim 1, wherein said sample preparation compartment further includes a capture region in fluid communication with said microchannel.

4. The integrated nucleic acid analysis system of claim 1, wherein said reaction zone comprises an immobilized catalyst.

5. The integrated nucleic acid analysis system of claim 4, wherein said immobilized catalyst comprises an activity to effectuate a predetermined structural modification of an oligonucleotide analyte or to amplify the amount of said oligonucleotide analyte to a detectable level for MALDI-TOF mass spectroscopy.

6. The integrated nucleic acid analysis system of claim 5, wherein said immobilized catalyst amplifies the amount of an oligonucleotide analyte.

7. The integrated nucleic acid analysis system of claim 6, adapted for PCR amplification, wherein said immobilized catalyst comprises a thermophilic DNA polymerase and said analysis system further includes means for rapidly cycling the temperature of said reaction zone as required for PCR amplification.

8. The integrated nucleic acid analysis system of claim 1, wherein said MALDI ionization surface is fabricated within said sample preparation compartment and is positioned for receiving an oligonucleotide analyte from said communicating microchannel and presenting said analyte to a mass spectrometer for MALDI-TOF mass spectral analysis.

9. The integrated nucleic acid analysis system of claim 8, wherein said MALDI ionization surface includes a reaction zone.

10. The integrated nucleic acid analysis system of claim 8, wherein said MALDI ionization surface includes a capture region.

11. The integrated nucleic acid analysis system of claim 9 or 10, wherein said connecting microchannel includes reversible sealing means.

12. The integrated nucleic acid analysis system of claim 1, wherein said MALDI ionization surface is included in a rotatable comb device comprised of an upper handle with downwardly extending teeth, whereupon the rotation of said device to a first position places said ionization surface in fluid communication with said microchannel and the rotation of said device to a second position aligns said ionization surface with the vacuum gate of a mass spectrometer for insertion therein.

13. The integrated nucleic acid analysis system of claim 12 wherein said comb teeth comprise hollow open-ended tubes coextensive with said comb handle, and said comb handle comprises a MALDI ionization surface.

14. The integrated nucleic acid analysis system of claim 12 wherein said comb teeth comprise wicks that each include an analyte capture region, and said capture region is coextensive with said MALDI ionization surface.

15. An integrated nucleic acid analysis system for MALDI-TOF mass spectrometry comprising a thin film support having
   (a) sample preparation compartment for receiving and handling oligonucleotide analytes, said compartment including a plurality of temperature-controlled reaction zones interconnected by microchannels to wells and capture regions, wherein said microchannels are provided with means for directing the flow of reagents and oligonucleotide analytes within said compartment and with sealing means, and said wells and capture regions are optionally provided with access ports, and one or more MALDI ionization surfaces fabricated within said compartment to communicate with at least one of said microchannels for receiving and presenting said oligonucleotide analytes to a mass spectrometer for MALDI-TOF mass spectral analysis;

(b) an access port communicating with at least one microchannel in said sample preparation compartment; and (c) automatable means for moving said oligonucleotide analytes within said compartment.

16. An integrated nucleic acid analysis system for MALDI-TOF mass spectrometry comprising:

a thin film support having (a) a sample preparation compartment for receiving and handling oligonucleotide analytes, said compartment including a plurality of temperature-controlled reaction zones interconnected by microchannels to wells and capture regions within said compartment, (b) an access port communicating with at least one of said microchannels, wherein said microchannels are provided with means for directing the flow of reagents and oligonucleotide analytes within the sample preparation compartment, and said wells and capture regions are optionally provided with access ports, and (c) automatable means for moving said oligonucleotide analytes within said compartment; and a MALDI ionization surface included in a rotatable comb device, said device comprising an upper handle with downwardly extending teeth, whereupon the rotation of said device to a first position places said ionization surface in fluid communication with a microchannel for receiving said oligonucleotide analytes contained therein, and the rotation of said device to a second position aligns said ionization surface with the vacuum gate of a mass spectrometer for insertion therein.

17. The integrated nucleic acid analysis system of claim 16 wherein said comb teeth comprise hollow open-ended tubes coextensive with said comb handle, and said comb handle comprises a MALDI ionization surface.

18. The integrated nucleic analysis system of claim 17, wherein said MALDI ionization surface further includes a capture region.

19. The integrated nucleic acid analysis system of claim 16 wherein said comb teeth comprise solid wicks, each of said wicks comprise a MALDI ionization surface, and said ionization surface further includes a capture region.

* * * * *